United States Patent [19]

Thirugnanam

[11] Patent Number: 5,506,251
[45] Date of Patent: Apr. 9, 1996

[54] SYNERGISIC INSECTICIDAL COMPOSITIONS

[75] Inventor: Muthuvelu Thirugnanam, Langhorne, Pa.

[73] Assignee: Rohm and Haas Company, Philadelphia, Pa.

[21] Appl. No.: 340,574

[22] Filed: Nov. 16, 1994

[51] Int. Cl.$^6$ ............................. A01N 37/18; A01N 43/64
[52] U.S. Cl. ............................................ 514/383; 514/615
[58] Field of Search ...................................... 514/383, 615

[56] References Cited

U.S. PATENT DOCUMENTS

| | | | |
|---|---|---|---|
| 4,985,461 | 1/1991 | Hsu et al. | 514/615 |
| 5,330,984 | 7/1994 | Kung et al. | 514/239.5 |

FOREIGN PATENT DOCUMENTS 1640  2/1991  WIPO .

OTHER PUBLICATIONS

Worthing et al, The Pesticide Manual, p. 661 (1991).
Journal of Toxicology & Environmental Health, 38:199–223, 1993–Insecticide Synergists: Role, Importance, & Perspectives, C. B. Bernard et al.
Fundamentals of Insect Physiology, "A Wiley–Interscience publication", M. S. Blum, pp. 486–491 (1985).
The Encyclopedia of Biological Sciences, 2nd Edition, pp. 141, 472–473 (1970).
Biochemistry, 2nd Edition, 1981, The Molecular Basis of Cell Structure and Function, A. L. Lehninger pp. 713–714.

*Primary Examiner*—Allen J. Robinson
*Attorney, Agent, or Firm*—Thomas D. Rogerson; Michael B. Fein

[57] ABSTRACT

Insecticidal compositions comprising a cytochrome P450 enzyme inhibitor compounds and an N,N'-dibenzoyl-N'-tert-alkyl-hydrazine have been discovered which exhibit enhanced efficacy over composition with an N,N'-dibenzoyl-N'-tertalkylhydrazine alone.

3 Claims, No Drawings

SYNERGISIC INSECTICIDAL COMPOSITIONS

Insecticidal compositions are known which contain N,N'-dibenzoyl-N'-tert-alkylhydrazines, such as those described in U.S. Pat. No. 4,985,461. Although such compositions may be effective against some insects, there was a need for compositions which are more efficacious against a broader spectrum of insects and require lower amounts of N,N'-dibenzoyl-N'-tert-alkyl-hydrazine as a matter of conservation, environmental concern and cost.

Compositions comprising a cytochrome P450 enzyme inhibitor compounds and an N,N'-dibenzoyl-N'-tert-alkyl-hydrazine exhibit synergistic activity as insecticides.

Preferably, the N,N'-dibenzoyl-N'-tert-alkyl-hydrazine is selected from unsubstituted N,N'-dibenzoyl-N'-tert-alkyl-hydrazine or substituted N,N'-dibenzoyl-N'-tert-alkyl-hydrazine having the formula N-(2-A-3-B-4-C-benzoyl)-N'-(3-D-5-E-benzoyl)-N'-tert-alkyl-hydrazine, wherein A, B, and C are substituent groups independently selected from hydro; $(C_1-C_4)$alkyl, preferably methyl or ethyl; $(C_1-C_4)$alkoxy, preferably methoxy or ethoxy; and halo, preferably bromo, chloro or fluoro; and D and E are substituent groups independently selected from hydro and $(C_1-C_2)$alkyl, preferably methyl. More preferably, the substituents groups A, B, and C are selected independently from methoxy, ethoxy, methyl or ethyl. The tert-alkyl group of the N'-tert-alkyl substituent is preferably a tert-$(C_4-C_6)$alkyl, more preferably tert-butyl. Preferred N,N'-dibenzoyl-N'-tert-butyl-hydrazines are N-(2,3-dimethylbenzoyl)-N'-(3,5-dimethylbenzoyl)-N'-ter-butyl-hydrazine: N-(4-ethylbenzoyl)-N'-(3,5dimethylbenzoyl)-N'-tert-butyl-hydrazine or N'-(3,5-dimethylbenzoyl)-N-(2-methyl-3-methoxybenzoyl)-N'-tert-butyl-hydrazine.

The cytochrome P450 enzyme inhibitor usable in the present invention is selected from methylenedioxyphenyl compounds (such as sesamin, myristicin, apiol, sesamolin, tropital, piperonyl butoxide, sulfoxide, and propyl isome), sesamex, dillapiol, sesamine, N-decylimidazole and WARF-antiresistant as well as imidazoles, morpholines, pyrimidines and triazoles. The cytochrome inhibitor is preferably selected from imidazoles, morpholines, pyrimidines and triazoles.

Preferred imidazoles are 1[(1,1'-biphenyl)-4-ylphenylmethyl]-1H-imidazole (e.g. bifonazole); 1-[(2-chlorophenyl)diphenylmethyl]-lH-imidazole (e.g. clotrimazole); 1-[2-(2, 4-dichlorophenyl)-2-propenyloxy)ethyl]-1H-imidazole (e.g. imazalil); cis-1-acetyl-4-[4-[[2-(2,4-dichlorophenyl)-2-(1H-imidazole-1-ylmethyl)-1,3-dioxolan-4-yl]-methoxyphenyl [piperazine (e.g. ketoconazole); 1-[2-(2,4-dichlorophenyl)-2-[(2-(2,4dichlorophenyl)methoxy]ethyl]-1H-imidazole (e.g. micronazole); 1-(N-propyl-N-(2-(2,4,6-trichlorophenoxyl) ethyl)carbamoyl)imidazole (e.g. prochloraz). The more preferred imidazole is prochloraz.

A preferred morpholine is (+,–)-cis-4-[3-(4-tert-btylphenyl)-2-methylpropyl]-2,6-dimethylmorpholine (e.g. fenpropimorph).

A preferred pyrimidine is 3-(2-chlorophenyl)-3-(4-chlorophenyl)-5-pyrimidinemethanol (e.g. fenarimol, also described as (+,–)-2,4'-=dichloro-alpha-(pyrimidin-5-yl-)benzhydryl alcohol).

Preferred triazoles are 1-[[2-(2,4-dichlorophenyl)-1,3-dioxolan-2-yl]methyl]-1H-1,2,4-triazole (e.g. azaconazole); (E)-(RS)-1-(2,4-dichlorophenyl)-4,4-dimethyl-2-(1H-1,2,4-triazole-1-yl)-pent-1-3-ol (e.g. diniconazole); (+,–)-alpha-[2-(4-chlorophenyl)ethyl)]alpha-phenyl-(1H-1,2,4-triazole)-1-propanitrile (e.g. fenbuconazole); alpha-(2,4-difluorophenyl)-alpha-(-(1H-1,2,4-triazol-1-ymlethyl)-1H-1,2,4-trazol-1-ethanol (e.g. fluconazole); (RS)-2-(2,4-dichlorophenyl)-1-(1H-1,2,4-triazol-1-yl)-hexan-2-ol (e.g. hexaconazole); 4-[4-[4-[4-[2-(2,4-dichlorophenyl)-2-1H-1, 2,4-triazol-1-ylmethyl)-1,3-dioxolan-4-yl]-methoxypehnyl-1-peperazinyl]phenyl]-2,4-dihyro-2-(1-methylpropyl)-3H-1,2,4-trazol-3-one (e.g. itraconazole); alpha-butyl-alpha-(4-chlorophenyl)-1H-1,2,4- trazole-1-propanitrile (e.g. myclobutanil); 1-(2,4-dichloro-beta-propylphenethyl)-1H-1,2,4-triazole (e.g. penconazole); and (+,–)-=1-[[2-(2,4-dichlorophenyl)-4-propyl-1,3-dioxiolan-2-yl]methyl]-1H-1, 2,4-triazole (e.g. propiconazole). The more preferred triazoles are dirdconazole, fenbuconanzoles, hexaconazole, myclobutanil, and propiconazole.

The relative proportion of the amount of cytochrome P450 enzyme inhibitor compounds to N,N'-dibenzoyl-N'-tert-alkyl-hydrazine compounds in the embodied composition is that proportion of amount which exhibits unexpected synergistic efficacy as an insecticide. In some embodied compositions, the presence of a combination of one or more cytochrome P450 enzyme inhibitor compounds and one or more N,N'-dibenzoyl N'-tert-alkyl-hydrazines is associated with an enhanced efficacy such that insecticidai activity is unexpectedly present as compared to the efficacy of the composition without any cytochrome P450 enzyme inhibitor compound, such composition without any cytochrome P450 enzyme inhibitor compound exhibiting little or substantially no efficacy as an insecticide. In other embodied compositions, the composition with N,N'- dibenzoyl-N'-tert-alkyl-hydrazine exhibits significant insecticidal activity without any cytochrome P450 enzyme inhibitor compound but combining the cytochrome P450 enzyme inhibitor compound with the N,N'-dibenzoyl-N'-tert-alkyl-hydrazine composition exhibits a significantly enhanced insecticidal activity or efficacy.

For such compositions the synergistic relative proportions by weight of the amount of cytochrome P450 enzyme inhibitor compounds to N,N'-dibenzoyl-N'-tert-alkyl-hydrazine compounds preferably ranges from 0.1:1 to about 1000:1. Conveniently the range is at least about equal (i.e., 1:1), preferably at least 5 times as much (5:1), more preferably at least one hundred times as much. The ranges of proportions have practical upper limitations depending upon the particular application involved and would normally be expected to be at that particular proportion of complete kill for the amount of N,N'-dibenzoyl-N'-tert-alkyl-hydrazine compound used, but the maximum proportion of cytochrome P450 enzyme inhibitor compounds to hydrazine is not critical otherwise.

Preferred compositions comprise one or more N,N'-dibenzoyl-N'-tert-alkyl-hydrazine compounds, preferably N-(2,3-dimethylbenzoyl)-N'-(3,5-dimethylbenzoyl)-N'-tert-butyl-hydrazine, N'-(3,5-dimethylbenzoyl)-N-(4-ethylbenzoyl)-N'-tert-butyl-hydrazine or N'-(3,5-dimethylbenzoyl)-N-(2-methyl-3-methoxybenzoyl)-N'-tert-butyl-hydrazine, and one or more cytochrome P450 enzyme inhibitor compound selected from diniconazole, fenarimol, fenbuconazole, fenpropimorph, myclobutanil, prochloraz and propiconazole, in synergistic ratios wherein the amount of inhibitor is effective to significantly enhance the insecticidal activity of the composition relative to the composition without the inhibitor.

The embodied compositions of the present invention can be used in agronomically acceptable compositions or formulations. Such agronomically acceptable compositions can be used to dissolve, disperse of diffuse the embodied compositions without impairing the active ingredients effectiveness and which by itself has no significant detrimental effect on the soil, equipment, desirable plants, or agronomic environment. If desired, adjuvants such as surfactants, stabilizers, antifoam agents and antidrift agents may also be combined, as well as herbicides, fungicides and other agrichemically active materials used for their expected utility.

Accordingly, the embodied compositions of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth regulating agents, or other synergists.

The active compounds can be applied as insecticide sprays by methods commonly employed, such as conventional high-gallonage hydraulic sprays, low-volume sprays, airblast spray, aerial sprays, and dusts. commonly employed, such gallonage sprays, ultra-low-volume sprays, airblast spray, aerial sprays, and dusts.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added adhesives such as polyvinylalcohol-cellulose derivatives or other colloidal materials, such as casein, to improve the adherence of the pesticide to the surface to be protected.

Another embodiment of the present invention is a method for controlling insects comprising applying embodied compositions to the soil or foliage where it is absorbed by the plant, translocated to other plant parts and ultimately ingested by the pest or insects by means of ingestion of the plant part(s). This means of application is referred to as "systemic" application. Alternatively, the embodied compositions may be applied to the soil and contacted therein with the insects and other pests to be controlled. This means of application is referred to as "soil" application. In another alternative, the embodied compositions may be foliarly applied to the plants to be fred from insects and other pests which feed on the foliage.

In this regard then the present invention also contemplates a method of killing, combating or controlling insects which comprises contacting insects with a combative or toxic amount (i.e. pesticidally effective amount) of at least one composition comprising a first amount of an N,N'-dibenzoyl-N'-tert-alkyl-hydrazine and a second amount of a cytochrome P450 enzyme inhibitor, wherein said second amount of inhibitor is effective to significantly enhance the insecticidal activity of said hydrazine. The embodied composition can be applied alone or together with a carrier vehicle as noted above. The term "contacting" as employed in the specification and claims means applying to at least one of (a) such insects and (b) the corresponding habitat thereof (i.e., the locus to be protected, for example, to a growing crop or to an area where a crop is to be grown) the embodied composition of this invention alone or as a constituent of a larger composition or formulation.

The following examples are intended to illustrate the present invention but are not intended to limit the scope thereof.

EXAMPLE 1

Test Against The Larvae Of Southern Armyworm
(*Spodoptera Eridania*).

A flowable formulation of N'-(3,5-dimethylbenzoyl)-N-(4-ethylbenzoyl)-N'-tert-butyl-hydrazine containing 23% active ingredient (a.i.) is diluted with water to get a 2.5 parts per million by weight (ppmw) a.i. aqueous solution. To this solution, the required quantifies of a composition of 0.5 pounds of fenbuconazole per gallon of water emulsion concentrate formulation are added to get 0, 62.5, 125, and 250 ppmw a.i. fenbuconazole in respective solutions. Aqueous fenbuconazole solutions containing 0, 62.5 125, and 250 ppmw a.i. without adding N'-(3,5-dimethylbenzoyl)-N-(4-ethylbenzoyl)-N'-tert-butylhydrazine are also prepared. All solutions are sprayed onto lima bean (*Phaseolus lunatus*) plants using a 3 nozzle-boom containing TX-1 nozzle tips at 40 psi pressure to give 30 gallon/acre rate. After the spray deposits are air-dried, the treated leaves are detached from the plants, placed in petri dishes and infested with third instar larvae of southern armyworm (*Spodoptera eridania*). After 4 days, the number of dead caterpillars are counted and the percent mortality ratio is calculated.

The results are summarized below in Table 1 which shows synergistic enhancement of the insecticidal activity of N'-(3,5-dimethylbenzoyl)-N-(4-ethylbenzoyl)-N'-tert-butylhydrazine vs. Southern armyworm by combination with fenbuconazole, a cytochrome P450 enzyme inhibiting ergosterol biosynthesis-inhibiting fungicide.

TABLE 1

| Solution No | Treatment | % Control |
|---|---|---|
| | Control of Southern Armyworm | |
| 1. | N'-(3,5-dimethylbenzoyl)-N-(4-ethyl-benzoyl)-N'-tert-butylhydrazine-2.5 ppmw | 11 |
| 2. | Solution No. 1 + fenbuconazole-62.5 ppmw | 22 |
| 3. | Solution No. 1 + fenbuconazole-125 ppmw | 78 |
| 4. | Solution No. 1 + fenbuconazole-250 ppmw | 78 |
| 5. | fenbuconazole - 0 ppmw | 0 |
| 6. | fenbuconazole - 62.5 ppmw | 0 |
| 7. | fenbuconazole - 125 ppmw | 0 |
| 8. | fenbuconazole - 250 ppmw | 0 |

EXAMPLE 2

Test Against The Larvae Of Soybean Looper
(*Trichoplusis Includens*),

A flowable formulation of N'-(3,5-dimethylbenzoyl)-N-(4-ethylbenzoyl)-N'-tert-butyl-hydrazine containing 23% active ingredient is diluted with tap water to give 0, 5, 10 and 20 ppmw a.i. solutions. A similar set of solutions is prepared from N'-(3,5-demethylbenzoyl-N-(4-ehylbenzoyl)-N'-tert-butyl-hydrazine using 150 ppmw a.i. aqueous solution of myclobutanil instead of plain tap water. A third set of solutions is also prepared from N'-(3,5-dimethylbenzoyl-N-(4-ethylbenzoyl)-N'-tert-butyl-hydrazine using 150 ppmw a.i. aqueous solution of fenbuconazole. The 3 sets of solutions are separately sprayed onto detached soybean (Glycine max) leaves contained in petri dishes at 100 gallons/acre rate. After the spray deposit is air-dried, the treated leaves are infested with third instar soybean looper larvae at 10 larvae/dish. After 3 days of infesting, the dead caterpillars are counted in each treatment and the results are expressed as percent mortality ratio in Table 2 which shows synergistic. enhancement of the insecticidal activity of N'-(3,5-dimethyl-benzoyl)-N-(4-ethylbenzoyl)-N'-tert-butylhydrazine vs. Soybean looper by combination with mydobutanil and fenbuconzaole, cytochrome P450 inhibiting ergosterol-biosynthesis inhibitory fungicides.

TABLE 2

Control of Soybean Looper

| Solution No | Treatment | % Control |
|---|---|---|
| 1. | N'-(3,5-dimethylbenzoyl)-N-(4-ethyl-benzoyl)-N'-tert-butylhydrazine-5 ppmw | 0 |
| 2. | Solution No. 1 + myclobutanil - 150 ppmw | 50 |
| 3. | Solution No. 1 + fenbuconazole-150 ppmw | 100 |
| 4. | Myclobutanil - 150 ppmw | 0 |
| 5. | fenbuconazole - 150 ppmw | 0 |

EXAMPLE 3

Inhibitors Exhibiting Synergy Against The Larvae of Soybean Looper (*Trichoplusis Includens*).

A 23% flowable formulation of N'-(3,5-dimethylbenzoyl)-N-(4-ethylbenzoyl)-N'-tert-butyl-hydrazine is diluted with tap water to give 5 ppmw a.i. solution. Similar solutions of the hydrazine insecticide are also prepared using 30 ppmw a.i. solution of several inhibitors such as diniconazole, fenbuconazole, propiconazole, hexaconazole (triazole fungicides), prochloraz (imidazole fungicide), fenarimol (pyrimidine fungicide) and fenpropimorph (morpholine fungicide). The test is conducted as described in Example 2 against soybean looper larvae. The results are summarized in Table 3 which shows synergistic enhancement of the insecticidal activity of N'-(3,5-dimethylbenzoyl)-N-(4-ethylbenzoyl)-N'-tert-butylhydrazine vs. Soybean looper with other ergosterol biosynthesis-inhibiting fungicides.

TABLE 3

Control of Soybean Looper

| Solution No | Treatment | % Control |
|---|---|---|
| 1. | N'-(3,5-dimethylbenzoyl)-N-(4-ethyl-benzoyl)-N'-tert-butylhydrazine-5 ppmw | 20 |
| 2. | Sample No. 1 + diniconazole - 30 ppmw | 100 |
| 3. | Sample No. 1 + fenbuconazole - 30 ppmw | 100 |
| 4. | Sample No. 1 + propiconazole - 30 ppmw | 80 |
| 5. | Sample No. 1 + hexaconazole - 30 ppmw | 30 |
| 6. | Sample No. 1 + prochloraz - 30 ppmw | 90 |
| 7. | Sample No. 1 + fenarimol - 30 ppmw | 70 |
| 8. | Sample No. 1 + fenproprimorph-30 ppmw | 50 |
| 9. | diniconazole - 30 ppmw | 0 |
| 10. | fenbuconazole - 30 ppmw | 0 |
| 11. | propiconazole - 30 ppmw | 0 |
| 12. | hexaconazole - 30 ppmw | 0 |
| 13. | prochloraz - 30 ppmw | 0 |
| 14. | fenarimol - 30 ppmw | 0 |
| 15. | fenpropimorph - 30 ppmw | 0 |
| 16. | Blank (water without any active ingredient) | 0 |

EXAMPLE 4

Using Cytochrome P450 Enzyme Inhibitory and Sesamol

Against the larvae of Southern armyworm (*Spodoptera eridania*)

A 23% flowable formulation of N'-(3,5-dimethylbenzoyl)-N-(4-ethylbenzoyl)-N'-tert-butyl-hydrazine is diluted with tap water to give 5 ppmw a.i. solution. Similar solutions of hydrazine insecticide are also prepared using 4 ppmw a.i., 40 ppmw a.i., and 400 ppmw a.i. solutions of Sesamol, a methylenedioxy benzene derivative and a known inhibitor of cytochrome P450 enzyme. This test is conducted as described in Example 2 against 3rd instar Southern armyworm larvae. The % insect control determined 4 days after treatment are summarized in Table 4 which shows enhancement of the insecticidal activity of N'-(3,5-dimethylbenzoyl)-N-(4-ethylbenzoyl)-N'-tert-butylhydrazine vs. Southern armyworm with Sesamol, a known cytochrome P450 enzyme inhibitor.

TABLE 4

Control of Southern Armyworm

| Solution No | Treatment | % Control |
|---|---|---|
| 1. | N'-(3,5-dimethylbenzoyl)-N-(4-ethyl-benzoyl)-N'-tert-butylhydrazine-5 ppmw | 11 |
| 2. | Solution No. 1 + Sesamol - 4 ppmw | 28 |
| 3. | Solution No. 1 + Sesamol - 40 ppmw | 33 |
| 4. | Solution No. 1 + Sesamol - 400 ppmw | 67 |
| 5. | Sesamol - 4 ppmw | 0 |
| 6. | Sesamol - 40 ppmw | 0 |
| 7. | Sesamol - 400 ppmw | 0 |

What is claimed is:

1. A synergistic insecticidal composition comprising synergistic effective amounts of N'-(3,5-dimethylbenzoyl)-N-(4-ehylbenzoyl)-N'-tert-butylhydrazine and a cytochrome P450 enzyme inhibitor selected from the group consisting of fenbuconazole and myclobutanil, wherein the weight ratio of the hydrazinc to P450 enzyme inhibitor is 1:0.1 to 1:1000.

2. A method of controlling insects which comprises contacting insects with a synergistic insecticidally effective amount of the composition of claim 1

3. The method according to claim 2 wherein said insects are one or more of *Spodoptera Eridania* and Trichoplusis Includens.

* * * * *